United States Patent
Laustsen et al.

(10) Patent No.: US 11,390,839 B2
(45) Date of Patent: Jul. 19, 2022

(54) BIOREACTOR SYSTEM AND METHOD FOR PRODUCING A BIOPOLYMER

(71) Applicant: CMC Biologies A/S, Soeborg (DK)

(72) Inventors: Mads Laustsen, Gentofte (DK); Adrian Blackburn, Charlottenlund (DK)

(73) Assignee: CMC Biologies A/S, Soeborg (DK)

( * ) Notice: Subject to any disclaimer, the term of this patent is extended or adjusted under 35 U.S.C. 154(b) by 0 days.

(21) Appl. No.: 15/972,146

(22) Filed: May 5, 2018

(65) Prior Publication Data

US 2018/0251716 A1  Sep. 6, 2018

Related U.S. Application Data

(63) Continuation of application No. 15/037,765, filed as application No. PCT/EP2014/075019 on Nov. 19, 2014, now abandoned.

(30) Foreign Application Priority Data

Nov. 20, 2013 (EP) ..................... 13193679

(51) Int. Cl.
| | |
|---|---|
| C12M 1/00 | (2006.01) |
| C12P 21/02 | (2006.01) |
| C12M 1/12 | (2006.01) |
| C12M 1/34 | (2006.01) |

(52) U.S. Cl.
CPC ............ *C12M 29/10* (2013.01); *C12M 37/02* (2013.01); *C12M 41/26* (2013.01); *C12P 21/02* (2013.01)

(58) Field of Classification Search
CPC ....................................... C12M 29/10
USPC ....................................... 435/283.1
See application file for complete search history.

(56) References Cited

U.S. PATENT DOCUMENTS

| | | | | | |
|---|---|---|---|---|---|
| 4,264,740 | A | * | 4/1981 | Christ | A23J 1/16 210/208 |
| 4,473,970 | A | * | 10/1984 | Hills | C12N 1/12 47/1.4 |
| 5,362,642 | A | * | 11/1994 | Kern | B67D 7/0288 222/94 |
| 2006/0252145 | A1 | * | 11/2006 | House | C12M 99/00 435/289.1 |
| 2012/0088296 | A1 | * | 4/2012 | Vargas | C12M 23/06 435/292.1 |
| 2012/0156783 | A1 | * | 6/2012 | Kubiak | B01F 3/0803 435/404 |
| 2013/0112624 | A1 | * | 5/2013 | Gebauer | B01D 15/12 210/656 |

(Continued)

OTHER PUBLICATIONS

Trick, Algal Chemostats (Abstract), Comprehensive Biotechnology (Third Edition), vol. 4, 2011 (Year: 2011).*

(Continued)

*Primary Examiner* — Holly Kipouros
(74) *Attorney, Agent, or Firm* — Cheryl H. Agris; Agris & von Natzmer, LLP

(57) ABSTRACT

Provided is a bioreactor system and a fermentation process employing continuous inline medium dilution in which concentrated medium and nutrients are blended with water or buffer and fed to the cell culture vessel of a bioreactor system, e.g. for production of antibodies and other recombinant proteins by mammalian cells.

31 Claims, 2 Drawing Sheets

(56) References Cited

U.S. PATENT DOCUMENTS

2013/0323841 A1* 12/2013 Kruglick ................ C12M 25/00
                                                        435/402
2015/0118753 A1*  4/2015 Brau ...................... C12M 23/26
                                                        435/394
2015/0232505 A1   8/2015 Konstantinov

OTHER PUBLICATIONS

Related EP appln. No. 14799795.1, response to communication dated Apr. 3, 2019, submitted Jul. 25, 2019.
Related EP appln. No. 14799795.1, communication dated Jul. 25, 2019.
Parent U.S. Appl. No. 15/037,765 Office Action dated Nov. 6, 2018.
Related EP appln. No. 14799795.1, communication dated Apr. 21, 2021.

* cited by examiner

BIOREACTOR SYSTEM AND METHOD FOR PRODUCING A BIOPOLYMER

FIELD OF THE INVENTION

The present invention relates to a bioreactor system and a method for producing cells or a biopolymer using the bioreactor system. The methods of the present invention are suitable for use in a manufacturing process for preparing a polypeptide, in particular for preparing an active pharmaceutical ingredient for a pharmaceutical product.

BACKGROUND OF THE INVENTION

Traditionally, bacterial, yeast and mammalian cells for e.g. protein production are primarily cultured as suspension cultures in bioreactors, also called fermenters. In such bioreactors the environmental conditions can be precisely controlled by manipulating the supply of nutrients to the cells and the removal of waste materials, and a stirring means may stir the culture medium within the reactor to provide for a homogeneous distribution of the cells.

The bioreactor may be operated as a closed system in a batch or fed-batch process or as a continuous system in a so-called chemostat or perfusion process.

In a batch operation the culture medium usually contains a medium with the necessary nutrients, for example glucose, vitamins, amino acids and minerals. During fermentation, these are consumed so that the medium becomes more and more deprived in nutrients. At the same time, the concentration of waste products increases, which ultimately results in inhibition of cell growth. In a fed-batch process one or more of the nutrients are fed (supplied) to the bioreactor during cultivation to achieve better growth conditions and higher cell densities.

In a continuous system such as a chemostat fresh medium is continuously added, while culture liquid is continuously removed to keep the culture volume constant. By changing the rate at which medium is added to the bioreactor, the growth rate of the microorganism cells can be controlled. For cells with a high growth rate such as yeast and bacteria cells, the chemostat typically removes cells from the medium along with the culture liquid in order to maintain a desired cell density.

A perfusion process is a special type of continuous process in which a suspension cell culture is continuously supplied with fresh medium to the bioreactor while spent culture media is continuously harvested. The cells are continuously filtered or otherwise separated from the harvest stream and returned to the bioreactor to maintain a uniform cell density. The constant addition of fresh medium and elimination of waste products provides the cells with the optimal environment to achieve high cell concentrations and thus higher productivity. This allows prolonging healthy cultures, potentially at high cell density, as well as a short residence time of the product in the bioreactor. This is more favourable for product quality and is required for the production of unstable polypeptides. Another advantage of the perfusion mode is that it allows the use of smaller bioreactors compared with fed-batch processes, which provides benefits such as reduced clean-in-place operation and the possibility to use disposable bioreactors instead of stainless steel reactors due to the smaller working volumes. Moreover, product may be continuously harvested by taking out medium (with cells and product) or via a so-called bleed.

Due to an increasing demand for biologically produced medicinal products such as complex polypeptides, including antibodies and other recombinant proteins, perfusion processes are becoming a much more common production platform due to the high productivity in relation to the size of the bioreactor.

However, in large-scale continuous processes, media and harvest logistics require specific attention. Depending on the scale of the bioreactor and the chosen perfusion rate, it may be necessary to provide several bioreactor volumes of fresh medium daily to the bioreactor, e.g. 500 L to 6000 L or more, and to collect a similar daily volume for downstream purification. Thus, huge amounts of fresh medium have to be prepared daily for large-scale production facilities, for example up to about 7500 L for a 2500 L reactor, which clearly involves practical/logistical as well as economic challenges. Since purchase and handling of the cell culture medium are some of the most expensive aspects of the production of mammalian cell products, there is an acute need for systems that can optimize medium use and handling for industrial large-scale bioreactor systems.

The present invention addresses the need for improved and more efficient utilization and handling of cell culture media in large-scale bioreactor systems, in particular in continuous fermentation processes, and for improving productivity in such bioreactor systems.

SUMMARY OF THE INVENTION

The present invention provides a bioreactor system and a fermentation process employing continuous inline medium dilution in which concentrated medium and nutrients are blended with water or buffer and fed to the cell culture vessel of a bioreactor system. This system provides several advantages, one advantage being that medium and nutrients can be mixed from concentrated solutions with water or buffer by inline dilution immediately prior to use, thereby significantly reducing the container size requirement and making the overall process more efficient. Another advantage is that different media components may be blended from independent stock solutions having different concentrations and/or which are kept at different temperatures. Further advantages will be apparent from the disclosure below.

One aspect of the invention relates to a bioreactor system for producing a product selected from a cell and a biopolymer expressed by a cell, and wherein the bioreactor system comprises:
- a cell culture vessel (5) comprising a product harvest module (6);
- optionally, a bleed outlet (9);
- a medium container (1; 2);
- a water and/or buffer supply (3); and
- an inline medium dilution system (4) for diluting concentrated medium from the medium container, the inline medium dilution system having an inlet and an outlet, wherein the inlet is in fluid communication with the medium container and the water/buffer supply, and wherein the outlet is in fluid communication with the culture vessel.

Another aspect of the invention relates to a method for producing a biopolymer using the bioreactor system disclosed herein, the method comprising:
(a) fermenting cells expressing the biopolymer in a suitable medium under suitable conditions to allow expression of the biopolymer by the cells,
(b) harvesting the biopolymer by removing medium comprising biopolymer and impurities via the product harvest module, and
(c) isolating the biopolymer from the harvested medium;

wherein, during fermentation, the method further comprises:

adding concentrated medium from a medium container and water or buffer from the water/buffer supply to an inlet of the inline medium dilution system to result in diluted medium, and feeding the diluted medium containing nutrients to the culture vessel through an outlet to replenish nutrients consumed by the cells and to compensate for medium removed for harvesting of the biopolymer.

In a further aspect, the invention relates to the use of a bioreactor system as described herein for producing a product selected from a cell and a biopolymer expressed by a cell.

Further objects of the present invention will become apparent in view of the present description, figures and claims.

DRAWING DESCRIPTION

DETAILED DESCRIPTION OF THE INVENTION

Figure 1:
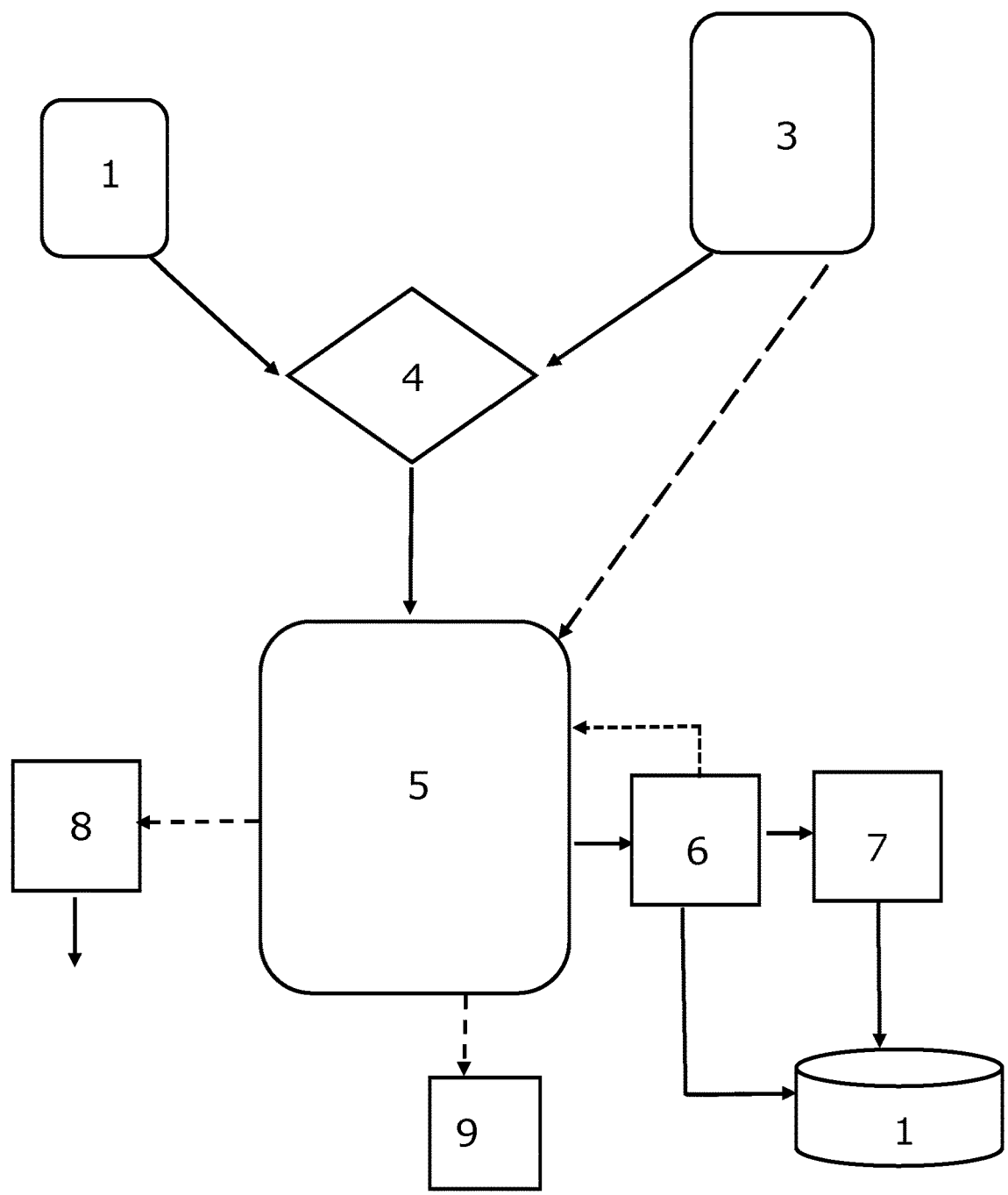
FIG. 1 is a schematic illustration of a basic bioreactor system of the invention.

The bioreactor system of the present invention includes several basic components, including a cell culture vessel comprising a product harvest module, at least one medium container, a water and/or buffer supply, an inline medium dilution system, and optionally a bleed outlet. It may also contain additional components such as an impurity filter unit. The characteristics of the individual components of the system, and their function in the context of the method of the invention for producing a biopolymer will be explained in detail in the following.

Bioreactor

As used herein the term "bioreactor" refers to any device or system that supports a biologically active environment, for example for cultivation of cells for production of a biological product. Bioreactors may range in size from a few liters to several cubic meters (i.e. several 1000 liters), and may be a conventional bioreactor based on a culture vessel of e.g. stainless steel or glass or a "single-use" bioreactor based on a disposable material such as a disposable bag.

While bioreactors have in the past typically been of the conventional type, most often based on stainless steel tanks, disposable bioreactors based on a disposable bag, typically made of a multilayer plastic material, are becoming more prevalent. For agitation, some single-use bioreactors use stirrers similar to those of conventional bioreactors, but with stirrers integrated into the plastic bag, while other single-use bioreactors are agitated by means of a rocking motion. Stirred single-use bioreactors may have a volume of up to several thousand liters, e.g. 2000 to 5000 liters, while rocking single-use bioreactors typically have a volume of up to about 1000 liters.

Single-use bioreactors have several advantages compared to conventional bioreactors, including reduced cleaning and sterilization demands, along with significant accompanying cost savings. In addition, complex qualification and validation procedures for pharmaceutical production can be simplified, and there is a reduced risk of cross contamination.

Further, since single-use bioreactors contain fewer parts compared with conventional bioreactors, initial and maintenance costs are reduced.

Based on the mode of operation, a bioreactor may be classified as batch, fed-batch or continuous. Examples of continuous bioreactors are a chemostat and a perfusion bioreactor. The bioreactor is typically equipped with one or more inlets for supplying culture medium to the cells, and with one or more outlets for harvesting product or emptying the bioreactor. Additionally, the bioreactor may be equipped with at least one outlet constructed in such a way that a separation device can be attached to the bioreactor. Typically, the bioreactor's environmental conditions such as gas (i.e., air, oxygen, nitrogen, carbon dioxide) flow rates, temperature, pH and dissolved oxygen levels, and agitation speed/circulation rate can be closely monitored and controlled.

The bioreactor may optionally also include a separate inlet for adding components such as vitamins or growth factors. In this case, such components may be added to the cell culture vessel in addition to the diluted medium, and may be either in concentrated or diluted form.

In a preferred embodiment, the bioreactor system of the invention is a continuous system, i.e. a perfusion or chemostat bioreactor. Perfusion bioreactors are typically used for cultivation of mammalian cells, while chemostat bioreactors are typically used for cultivation of microorganisms such as bacteria or yeast cells.

In an other embodiment the bioreactor system is a continuous production system.

Cell Culture Vessel

A "cell culture vessel" as used herein refers to an integral part of a bioreactor system in which cells are grown under suitable conditions in a suitable medium. The cell culture vessel may be a single-use vessel, e.g. a disposable bag, or a conventional reusable vessel, typically a stainless steel or glass vessel, as explained above. Stainless steel vessels are typically configured with predefined port assemblies, whereas single-use bags use pre-sterilized plastic cultivation chambers that are discarded after use. This eliminates space-consuming and expensive clean-in-place (CIP) and steam-in-place (SIP) installations while reducing production turn-around times.

The cell culture vessel of the invention typically has a volume of at least 50 L, preferably at least 100 L, more preferably at least 250 L, and still more preferably at least 500 L. In many cases, the volume will be still higher, e.g. at least 1000 L or at least 2000 L.

Medium Container

A "medium container" as used herein refers to any kind of container, e.g. a rigid tank of e.g. steel, glass or plastic or a collapsible and/or disposable bag, that holds cell culture medium and/or nutrients. In the context of the present invention, the medium container is connected to at least one inlet end of an inline dilution system, and the cell culture medium and/or nutrients will typically be present in the medium container in a more concentrated form than concentration of the same medium or nutrients when present inside the culture vessel.

In one embodiment of the invention, the bioreactor system may comprise two or more medium containers, each of which is in fluid communication with an inlet of the inline dilution system. The use of two or more medium containers may be advantageous in order to be able to further reduce container size, space requirements, etc., for example by using one container to hold medium components or nutrients having a relatively low solubility and another container to hold other medium components or nutrients that have a higher solubility. By having the low solubility components in a separate container, the volume of the container comprising the other components that have a higher solubility may be reduced. A further advantage of this approach is that components with a low solubility can be stored under conditions that contribute to increasing their solubility, for example by means of suitable pH adjustment. Medium and nutrients from the two or more medium containers can be mixed in suitable amounts via the inline medium dilution system in order to obtain a desired final culture medium composition. This is discussed in more detail further below in connection with the inline medium dilution system, from which it will be apparent that each medium container may be in direct or indirect fluid communication with an inlet of the inline medium dilution system.

In one embodiment at least one medium container in fluid communication with the inline dilution system has a volume of at least 10 L, such as at least 50 L, such as at least 100 L, e.g. at least 250 L.

In an embodiment, the concentrated medium in the medium container(s) may be kept at a reduced temperature of e.g. 1-10° C., such as about 5° C. In this case, the diluted medium is preferably pre-heated prior to being added to the culture vessel. This may be performed by heating the diluted medium as such or by mixing the concentrated medium with water/buffer that has been pre-heated to a desired temperature. For example, the diluted medium may be pre-heated to the same temperature as the temperature of the medium inside the culture vessel.

Inline Medium Dilution System

Inline dilution refers to the concept of mixing a concentrated solution and water (or some other diluent, e.g. an aqueous buffer in the present context) inside a processing line to produce a normal strength, process-ready solution. Inline dilution systems (sometimes called "on-site blending systems") also provide many advantages over purchasing pre-mixed and diluted cell culture media. By using a blending system, a single container or medium concentrate produces many times its volume in diluted medium. Thus, a single volume of concentrated medium, used to produce the equivalent of many volumes of dilute medium via the dilution system, greatly reduces facility costs associated with fabrication of large tanks, reduces floor space requirements, and reduces validation and quality control costs as well as spoilage and disposal costs of non-compliant, out-of-date or unused blended solutions. Costs associated with medium delivery and handling are also greatly reduced. In addition, onsite dilution and mixing increases the variety of medium concentrations and mixtures that are immediately available, without requiring a corresponding increase in the number of different types of media and nutrient supplements that must be purchased, thereby reducing facility and operating costs and providing the logistical and administrative advantage of reduced inventory.

Another advantage of inline dilution is that if, for example, one component of a medium is consumed at a faster rate at a high cell density than at a low cell density, the medium can be compensated for this by mixing in a higher concentration of this component.

Inline medium dilution of concentrated medium or nutrient solutions with water or buffer must be made within tight specification ranges for pH, conductivity, osmolality, and temperature, which are critical process parameters. This requires that a precise mixture of the concentrated solution and water can be delivered with minimal deviation over time. Also, the solution must be well mixed prior to delivery to the cell culture vessel.

The inline medium dilution system may, in its most basic form, be a simple system of tubes or pipes from which concentrated medium and water/buffer, respectively, are supplied, and that connect with each other at one end before being led into the inlet of the cell culture vessel. However, more typically the inline medium dilution system will be a more advanced automated system that allows two or more liquid streams to be brought together in a controlled fashion to meet a target diluted solution concentration. Inline dilution systems are commercially available from different suppliers such as from Novasep, GE Healthcare or for example the system IBD™ 1K Inline Buffer Dilution System from Asahi Kasei Bioprocess (disclosed in U.S. Pat. No. 8,271,139). Such systems are capable of making multi-component blends of up to 20× concentrates and produce a ready-to-use solution offering total blend flow rates of more than 1000 L/h.

As used herein, the term "water and/or buffer supply" or "water/buffer supply" is intended to encompass any supply of water or buffer for use in diluting the concentrated medium. This can include containers that hold water or a pre-mixed buffer solution for mixing with the concentrated medium as well as e.g. dilution systems in which a concentrated buffer is mixed with water prior to use in the inline medium dilution system. Further, in the event the inline medium dilution system dilutes the concentrated medium with water only, the water supply may be any supply of suitable water, whether stored in a tank or other container or supplied as needed in purified form using e.g. ultrafiltration or reverse osmosis.

In one embodiment of the present invention, the inline dilution system has a total blend flow rate of at least 1 L/min, such as at least 2 L/min, such as at least 5 L/min, such as at least 10 L/min.

There are several approaches for operating the blend procedure. For example, some systems blend the final solution based on conductivity and/or pH data provided by conductivity and pH process analyzers, whereas other systems use volumetric flow rate as the primary means of control, since inline pH and conductivity meters have an inherent tendency to drift and improper calibration may result in false readings.

The inline medium dilution system e.g. may be constructed such that all the media components and nutrients are pre-mixed into a single concentrated solution designed to be diluted with water or buffer by e.g. a factor of 1.5 or more, typically two or more, for example a factor of three, a factor of four or a factor of five, or even higher, such as factor of eight or ten, in the inline dilution system and subsequently provided to the cell culture vessel. In this case, the system will use a single medium container.

Alternatively, the system may employ two or more medium containers, e.g. containing different medium components with different solubilities as discussed above. In this case, the system may be constructed such that different media components and nutrients having different concentrations are led into a single mixing chamber by different inlets at different flow rates and diluted in the mixing chamber with water or buffer to the desired concentration (e.g. to the concentration of the medium in the cell culture vessel), whereafter the diluted mixture is provided to the cell culture vessel. Another option in the case of multiple medium containers is for each medium container to be connected to a separate mixing chamber for dilution with water or buffer. The separate mixing chambers can be further connected to a common mixing chamber, wherein diluted medium from two or more individual separate mixing chambers is mixed together before being led into the culture vessel via a single inlet, or alternatively, diluted medium from individual separate mixing chambers may be led into the culture vessel by way of multiple inlets, e.g. one inlet for each mixing chamber.

In one embodiment of the invention, the inline medium dilution system may be connected to a sensor located within or outside the cell culture vessel that can measure the concentration or the amount of medium or of selected components or nutrients in the cell culture vessel. The inline dilution system may in this case be operated as an automated system, allowing the concentration or the amount of medium or selected medium components or nutrients in the cell culture vessel to e.g. be kept constant in the event the perfusion rate is changed or a bleed is made to decrease the cell density in the cell culture vessel, or to otherwise be regulated as desired.

The inline medium dilution system may have inline monitoring and control of the dilution process using instrumentation such as mass flow meters and/or analytical instruments such as pH, conductivity or near-infrared (NIR) instrumentation. A programmable logic controller may integrate the operation and control of all components in the system.

If desired, a holding step can be used following mixing of the concentrated medium with the water/buffer to produce the diluted medium. The system of the invention may therefore optionally include a "holding container", e.g. a holding tank, between the inline medium dilution system and the cell culture vessel, i.e. such that outlet of the inline medium dilution system is in indirect fluid communication with the cell culture vessel. The holding tank/container may function not only to temporarily hold the diluted medium, but may also, if desired, be adapted to provide additional mixing of the diluted medium before it is led into the cell culture vessel. This may e.g. be advantageous when using multiple medium containers with e.g. one container for the low solubility components.

Product Harvest Module

In one embodiment the product harvest module is in its most simple form just an outlet leading to a container or bag suitable for collecting the product along with cells, impurities and medium for storage or further downstream processing. It may also be a separation device capable of, for example, separating polypeptides from cells, cell debris and impurities larger than the product of interest. The product harvest module may be operated to continuously harvest the product in a harvest stream that is collected for further downstream processing.

The product harvest module may also be a separation device such as a cell retention device that can separate cells from the product harvest stream such that the cells are retained in the cell culture vessel.

There are two major classes of techniques for the separation of cells from the medium, namely by gravitational or centrifugal sedimentation, or by filtration (for example tangential filtration such as alternating tangential-flow filters, e.g. axial rotation filtration or as spin filters, flow filters, vortex filters or cross flow filtration). In one embodiment, the product harvest module is a separation device based on gravitational or centrifugal sedimentation. In a preferred embodiment the product harvest module is a separation device based on alternating tangential-flow filtration.

Gravitational separation is an industrial method of separating two components, either a suspension or a dry granular mixture in which separation of the components by gravity is practical. This method can be used to separate out solids from a liquid mixture if the solids are not soluble in the liquid. The skilled person will know how to attach suitable gravitational separation devices to a bioreactor.

Centrifugal separation is another well-known technique to separate out particles in suspension. Commercially available separators utilizing centrifugal force for separation fall in one of two categories, rotary centrifuges or hydrocyclones. Hydrocyclones are operated by creating a physical vortex within a cylindrical vessel, generating centrifugal force. The heavier phase is forced to the outside portion of the fluid and the lighter fluid stays in the inside as a core. As the fluid continues flowing, the separated portions are directed to different outlets. Suitable centrifugal separation devices are known and commercially available, and use of these together with a bioreactor will be familiar to those skilled in the art.

In another embodiment the product harvest module is a filter unit, in which case the product harvest module may be referred to as a product filter. A product filter is often selected with a pore size in the range of from a nominal molecular weight cutoff (NMWC) of about 50,000 daltons (50 kDa) to about 2 m, such as from an NMWC of about 100,000 daltons (100 kDa) to a pore size of about 1 m.

As known to the skilled person, a suitable product filter cut-off will depend on the size of product of interest. In a preferred embodiment, the product filter has an NMWC pore size of at least about 1.5 times the MW of the biopolymer (e.g. polypeptide) of interest. For instance, if the MW of a polypeptide of interest is 100,000 (100 kDa) the preferred cut-off of the product filter will be an NMWC of at least 150,000 (150 kDa). More preferably, the product filter has an NMWC pore size of at least 2 times the MW of the polypeptide of interest.

When the cells present in the bioreactor reach a satisfactory cell density or when there is sufficient product present in the outflow through the harvesting outlet, harvest of the product may be initiated. This may be determined by measuring the cell density, for example using a spectrophotometer, or by measuring the amount of the product of interest by known means, for example using a suitable protein assay method in the case of a polypeptide product.

Impurity Filter Unit

Numerous specialized filters and filtration methods have been developed to separate materials according to their chemical and physical properties. Known filters include flat surface filters, pleated filters, multi-unit cassettes, and tubular forms such as hollow fibers. For the invention described herein any system of ultrafiltration technology can be applied as long as sterility can be ensured.

As used herein the term "impurities" refers to undesired chemical or biological compounds produced by the cells present in the bioreactor, or which arise from cells that die or break open during the fermentation process. Impurities include e.g. ethyl alcohol, butyl alcohol, lactic acid, acetone ethanol, gaseous compounds, peptides, lipids, ammonia, aromatic compounds, and DNA and RNA fragments, as well as media components.

Examples of filtration systems applicable for use in the production of polypeptides and removal of impurities as described herein are systems such as cartridge systems, plate and frame systems, and hollow fiber systems. The systems can be operated by pumping liquid over the membrane, by vibration (e.g. as supplied by PallSep™) or by alternating tangential flow (ATF), and both polymeric and ceramic membranes are well suited for the filtration process. A skilled person will be able to select a membrane with suitable properties.

Hollow fiber membranes have been successfully employed in a wide variety of industries, and have several benefits that include high membrane packing densities the ability to withstand permeate back-pressure, thus allowing flexibility in system design and operation. Hollow fiber cartridges can operate from the inside to the outside during filtration, allowing process fluid (retentate) to flow through the center of the hollow fiber and permeate to pass through the fiber wall to the outside of the membrane fiber. Tangential flow can help limit membrane fouling. Other operating techniques that can be employed with hollow fiber membrane systems include back flushing with permeate and retentate reverse flow.

Accordingly, the filter may be located in an external filter module attached to the bioreactor. Alternatively, the impurity filter may be located inside the bioreactor. The filter unit can also contain pumps or systems for preventing fouling of the filter such as an ATF system or the PallSep™ system in which controlled horizontal oscillation moves the membrane elements through the feed fluid. The oscillation generates vibrational energy at the membrane surface, giving shear (higher than that typically generated in conventional tangential flow filtration systems) that is limited to a small boundary layer above the membrane surface, and which is not applied to the bulk of the fluid. This ensures that even in high solids feed streams, the membranes do not cake with the retained species.

The system can, depending on the metabolites to be removed and the product in question, be equipped with membranes with a molecular weight cut-off value from a few hundred to tens of thousands. Often membranes with a cut-off between 1000 and 20,000 (1-20 kDa) are used. The benefit of using a membrane with a cut-off of about 10,000 (10 kDa) or below, preferably around 5000 (5 kDa), is that growth factors such as insulin and IGF-1 will be retained in the bioreactor.

During an extended run, it is possible to change the filters and resterilize the system without terminating the fermentation.

The skilled person will be able to select a suitable filter type for removal of impurities and a suitable membrane nominal molecular weight cutoff (NMWC) pore size with respect to allowing impurities to perfuse out of the impurity filter and harvest the polypeptide of interest through the product harvesting outlet.

In one embodiment, the impurity filter unit is selected from a membrane filter, a gravitational separation unit and a centrifugal separation unit.

The impurity filter is often selected with an NMWC within the range of 1000 to 30,000 (1-30 kDa), such as in the range of 2000 to 20,000 (2-20 kDa) or in the range of 2000 to 15,000 (2-15 kDa). However, if the product is a cell an impurity filter may be selected with an NMWC in the range of 1000 to 500,000 (1-500 kDa), but normally it is preferred that the impurity filter has a cutoff of less than 20,000 (20 kDa). Thus, in one embodiment the impurity filter unit is a membrane filter having an NMWC pore size of at least 1000, such as within the range of 2000 to 15,000.

In a preferred embodiment the impurity filter unit is a membrane filter having a molecular weight cut-off (NMWC) pore size of a maximum of 80% of the molecular weight (MW) of the product (e.g. polypeptide) of interest. For instance if the MW of the polypeptide of interest is 100,000 (100 kDa) the preferred maximum cut-off of the impurity filter will in this case be 80,000 (80 kDa). More preferably, the impurity filter has an NMWC pore size of a maximum of 50% of the MW of the polypeptide of interest. Thus, in one embodiment the impurity filter has a molecular weight cut-off (NMWC) pore size of a maximum of 80% of the MW of the biopolymer, such as a maximum of 50%.

Bleed Outlet

The "bleed outlet" is an outlet from the cell culture vessel that allows medium containing cells, cell debris and impurities to be removed from the cell culture vessel. It may be constructed as separate outlet, or it may be built together with the product harvest module. Bleeding of cells helps to ensure optimal productivity in continuous fermentation processes, in particular for perfusion processes, as it serves to e.g. improve overall cell culture viability, to avoid accumulation of dead cells and to prevent filter clogging. For cultures operated in perfusion mode it is a common practice to make bleeds daily if the viability of the cells drops to for example below 80% or when the cell density reaches a certain level, for example around 30 million cells/ml. During the bleeds up to 10% of the medium in the cell culture vessel may typically be removed, and this amount may increase with increasing cell density such that the bleeds may be used to regulate the cell density in the cell culture vessel.

While perfusion bioreactors will normally contain a bleed outlet, chemostat bioreactors used for e.g. bacteria or yeast cultivation generally do not include a bleed outlet.

Cell Culture Medium

As used herein "medium" refers to a cell culture medium. Numerous cell culture media are known and commercially available. Such media typically have a composition which is adapted for cultivation of certain types of cells and may comprise salts, amino acids, vitamins, lipids, detergents, buffers, growth factors, hormones, cytokines, trace elements and carbohydrates. Examples of salts include magnesium salts, for example $MgCl_2 \times 6H_2O$, and iron salts, for example $FeSO_4 \times 7H_2O$, potassium salts, for example $KH_2PO_4$, KCl, sodium salts, for example $NaH_2PO_4$ or $Na_2HPO_4$, and calcium salts, for example $CaCl_2 \times 2H_2O$. Examples of amino acids are the 20 naturally occurring amino acids, for example histidine, glutamine, threonine, serine, methionine. Examples of vitamins include ascorbate, biotin, choline, myo-inositol, D-panthothenate and riboflavin. Examples of lipids include fatty acids, for example linoleic acid and oleic acid. Examples of detergents include Tween® 80 and Pluronic® F68. An example of a buffer is HEPES. Examples of growth factors/hormones/cytokines include IGF, hydrocortisone and (recombinant) insulin. Examples of trace elements include Zn, Mg and Se. Examples of carbohydrates include glucose, fructose, galactose and pyruvate. Examples of other components that may be included in the medium are soy peptone and ethanol amine. The skilled person will be familiar with suitable media and media supplements as well as suitable conditions with respect to specific expression cells and polypeptides of interest.

Silicon-based antifoams and defoamers or nonionic surfactants such as coblock polymers of ethylene oxide/propylene oxide monomers may be added to the medium during fermentation.

The pH, temperature, dissolved oxygen concentration and osmolarity of the cell culture medium will depend on the particular type of cell, and will be chosen such that they are optimal for the growth and productivity of the cells in question. The person skilled in the art will know how to determine the optimal conditions such as pH, temperature, dissolved oxygen concentration and osmolarity for a given culture. Usually, the optimal pH for mammalian cells is between 6.6 and 7.6, the optimal temperature is between 30 and 39° C., and the optimal osmolarity is between 260 and 400 mOsm/kg. For microbial systems the pH may be between 3 and 8 and the temperature from 20 to 45° C.

The solubility of the different medium components varies considerably, as many of the components will have a high solubility and thus be easily dissolved in water whereas other components such as certain vitamins, amino acids, lipids and growth factors have a low solubility in water. For this reason, cell culture media are normally prepared by mixing together all the components as a ready-to-use composition.

In one embodiment of the present invention the medium is made such that components that are easily dissolved in water are prepared together in one lot, and components with a low solubility and that are difficult to dissolve in water are prepared together in another lot. The two (or more) lots are then separately dissolved in water so as to produce two (or more) concentrated media fractions having desired concentrations of the individual components. The concentrated media fractions may for example be prepared as solutions wherein the media components are 2 times, 3 times, 4 times, or 5 times or more, e.g. up to 10 times, as concentrated as the components in the culture vessel.

Cells

As used herein the term "cell" can include both prokaryotic and eukaryotic cells.

Expression of biopolymers, in particular polypeptides, for therapeutic use has been accomplished using bacteria, yeast and mammalian cells, and the skilled person will be familiar with numerous suitable expression cells for production of a given product. The cells expressing the biopolymer (e.g. polypeptide) may thus be selected e.g. from the group consisting of *E. coli, Bacillus*, yeast of the genus of *Saccharomyces, Pichia, Aspergillus, Fusarium*, or *Kluyveromyces*, CHO (Chinese hamster ovary) cells, hybridomas, BHK (baby hamster kidney) cells, myeloma cells, HEK-293 cells, PER.C6® cells, human lymphoblastoid cells and mouse cells, for example NS0 cells.

In the context of the present invention, the cells are preferably eukaryotic cells, in particular mammalian cells. Preferred cell lines typically employed for mammalian cell culture include CHO cells, NS0 cells, BHK cells, HEK-293 cells and PER.C6® cells. In one embodiment, the cell is a CHO cell such as a CHO DG44 cell, for example under control of Chinese hamster EF-1α regulatory sequences.

Since the invention as described preferably operates using a high cell density, one may advantageously use a cell culture medium with a high cell density from one fermentation to re-start (i.e. seed) a new fermentation. A high viable cell density in this context is typically a density of at least 10 million cells/ml, preferably at least 20 million cells/ml, more preferably at least 30 million cells/ml, e.g. at least 40 million cells/ml, such as at least 50 million cells/ml. A preferred cell density is from at least 10 million cells/ml to 100 million cells/ml such as from 10 million cells/ml to 80 million cells/ml.

In some cases, it may be convenient to grow cells to a desired cell density in one bioreactor and then transfer the cells to a second bioreactor for inducing the expression of the polypeptide by adding an inducer (for cells that are under control of an inducible promoter) or by changing the temperature and/or the pH of the medium. In such case impurities may also be removed via the separation device of the first bioreactor using a desired flow rate and via the separation device of the second bioreactor using the same or a different desired flow rate.

Biopolymers

The term "biopolymer" as used herein means a polypeptide, protein, nucleic acid or virus particle, which can be native or biologically or synthetically modified, including fragments, multimers, aggregates, conjugates, fusion products etc. In one embodiment, the biopolymer is a recombinant protein such as an antibody. In another embodiment, the biopolymer is a virus particle or part thereof, for example a protein coat, for use as a vaccine. In a further embodiment, the biopolymer may be a nucleic acid.

In a preferred embodiment of the present invention the product is a polypeptide or protein. As used herein, the terms "protein" or "polypeptide" may be used interchangeably and refer to any chain of amino acids, regardless of length or post-translational modification. Proteins can exist as monomers or multimers, comprising two or more assembled polypeptide chains, fragments of proteins, polypeptides, oligopeptides, or peptides.

Examples of polypeptides of interest that may be produced using the systems and methods of the invention include recombinant therapeutic proteins such as antibodies or fragments thereof, blood clotting factors, cytokines, enzymes, peptide hormones, etc. Specific examples of such proteins include human growth hormone, follicle-stimulating hormone, Factor VIII, Factor VII, Factor IX, erythropoietin (EPO), granulocyte colony-stimulating factor (G-CSF), alpha-galactosidase A, alpha-L-iduronidase (rhIDU; laronidase), N-acetylgalactosamine-4-sulfatase (rhASB; galsulfase), DNAse, tissue plasminogen activator (TPA), glucocerebrosidase, interferons (IF) such as interferon-alpha, interferon-beta and interferon-gamma, insulin, insulin derivatives, insulin-like growth factor 1 (IGF-1), tenecteplase, antihemophilic factor, human coagulation factor, and etanercept; and antibodies such as Trastuzumab, Infliximab, Basiliximab, Belimumab, Daclizumab, Adalimumab, Abciximab, Afutuzumab, Alemtuzumab, Cetuximab, Daclizumab, Denosumab, Eculizumab, Edrecolomab, Golimumab, Ibritumomab tiuxetan, Mepolizumab, Motavizumab, Natalizumab, Ofatumumab, Omalizumab, Oregovomab, Palivizumab, Pemtumomab, Pertuzumab, Ranibizumab, Rituximab, Tefibazumab and Zanolimumab.

In a particular embodiment of the present invention, the product is an antibody or a fragment thereof, where a fragment can e.g. be a Fab fragment, Fv fragment or single chain Fv (scFv) fragment.

Polypeptides are expressed under the control of regulatory sequences called promoter sequences. Cells expressing a polypeptide may be under the control of a constitutive promoter (i.e. unregulated sequences; this allows for continual transcription of the associated gene) or under control of an inducible promoter (regulatory sequences induced by the presence or absence of biotic or abiotic factors). In some cases, if the polypeptide of interest has limited stability or exhibits toxic effects on the host cell, it may be convenient to express it under control of an inducible promoter such that the cells first are grown to a desired cell density, after which expression of the polypeptide is induced by adding an inducer or by changing the temperature and or the pH of medium. An example of a constitutive promoter is a Chinese hamster EF-1α promoter. In one embodiment, the biopolymer is expressed under control of Chinese hamster EF-1α regulatory sequences.

By use of the system and method of the invention, it is possible to express polypeptides such as antibodies with high productivity. Thus, in one embodiment, the cells express a polypeptide, e.g. an antibody, and have a productivity of at least 1 gram/L/day, and preferably higher, such as 2 or 3 gram/L/day or more.

The isolated product (e.g. polypeptide) of interest produced using the system and method of the invention will be purified by methods known in the art for the given product, formulated into a final commercially relevant composition of interest (e.g. a pharmaceutical composition), and packaged in a suitable container.

Fermentation Process

As explained elsewhere herein, the system of the invention is preferably a continuous system, i.e. the fermentation is performed as continuous fermentation. In a preferred embodiment, the product produced by the method is a polypeptide, and the fermentation is performed as a perfusion process, i.e. a process in which a suspension cell culture in a bioreactor is continuously supplied with fresh medium while spent culture medium is continuously harvested, with cells being continuously filtered from the harvest stream and returned to the bioreactor to maintain a uniform cell density.

Except as otherwise described herein, the perfusion process may be performed as generally known in the art. A typical process may thus involve, following inoculation of the bioreactor, e.g. about 2-3 days in which the cells are grown without perfusion in order to obtain an initial desired cell density, followed by initiation of perfusion (i.e. harvest) at a low level of e.g. about 0.5-1 reactor volume per day, after which the perfusion rate is increased to e.g. about 1.5-3 reactor volumes per day once the cell density has increased further. The term "reactor volume" in this context will be understood as corresponding to the working cell culture vessel volume of the particular system. The process is continuously monitored as known in the art and as otherwise explained herein, such that growth conditions, medium concentration, cell density, pH etc. are maintained within desired specifications.

The level of the harvest stream for a given perfusion process, i.e. the level used for the majority of the fermentation, will be able to be determined by the skilled person taking into consideration the characteristics of the individual bioreactor system and process, but will often be in the range of from about 0.5 to about 3 reactor volumes per day, such as from about 1 to about 3 reactor volumes per day, e.g. from about 1.5 to about 2.5 reactor volumes per day. The perfusion process is often performed for about 3-6 weeks, but may last even longer, such as up to about 2 months or more.

Persons skilled in the art will be aware that the temperature of the medium in the cell culture vessel is a key factor for productivity of the cells, with a temperature in the range of about 30-38° C. often being optimal, and that it may be advantageous to employ a temperature reduction during the fermentation. Such procedures are well-known, in particular for mammalian cells such as CHO cells, and typically involve an initial fermentation phase at a first temperature of e.g. about 37° in order to obtain a desired cell density, followed by a reduction in temperature to, for example, about 32-35° for the remainder of the fermentation in order to increase expression of the polypeptide product and reduce cell division.

DETAILED DRAWING DESCRIPTION

The following non-limiting drawing descriptions are for example purposes only.

A bioreactor system of the invention in its basic form is illustrated schematically in FIG. 1, which shows a medium container (1) and a water/buffer container (3), both of which are in fluid communication with an inline medium dilution system (4). Concentrated medium from the medium container (1) is mixed in the inline medium dilution system (4) with water or buffer from the water/buffer container (3) in appropriate amounts to obtain a desired dilution of the concentrated medium. Diluted medium is then fed as needed to the cell culture vessel (5), which is where fermentation of the cells takes place in order to produce e.g. a polypeptide or other biopolymer. Water or buffer may in addition optionally be led directly from the water/buffer container (3) to the cell culture vessel (5) (illustrated by the dashed line between the two).

Connected to the cell culture vessel (5) is a product harvest module (6) for removing the biopolymer product along with cells, impurities and medium. The removed material may be led to a storage vessel (7) for temporary storage prior to being purified in the downstream processing (10), or it may be led directly from the harvest module (6) to the downstream processing (10). In a perfusion system, cells that are removed from the cell culture vessel (5) via the product harvest module (6) are typically returned to the cell culture vessel (5) (dashed line from (6) to (5)).

Connected to the cell culture vessel (5) is optionally also an impurity filter unit (8) for separating out undesired purities, and a optionally a separate bleed outlet (9) that allows medium containing cells, cell debris and impurities to be removed from the cell culture vessel (5). As explained above, the bleed outlet (9) may either be constructed as a separate unit or it may be built together as a single unit with the product harvest module (6).

Figure 2:
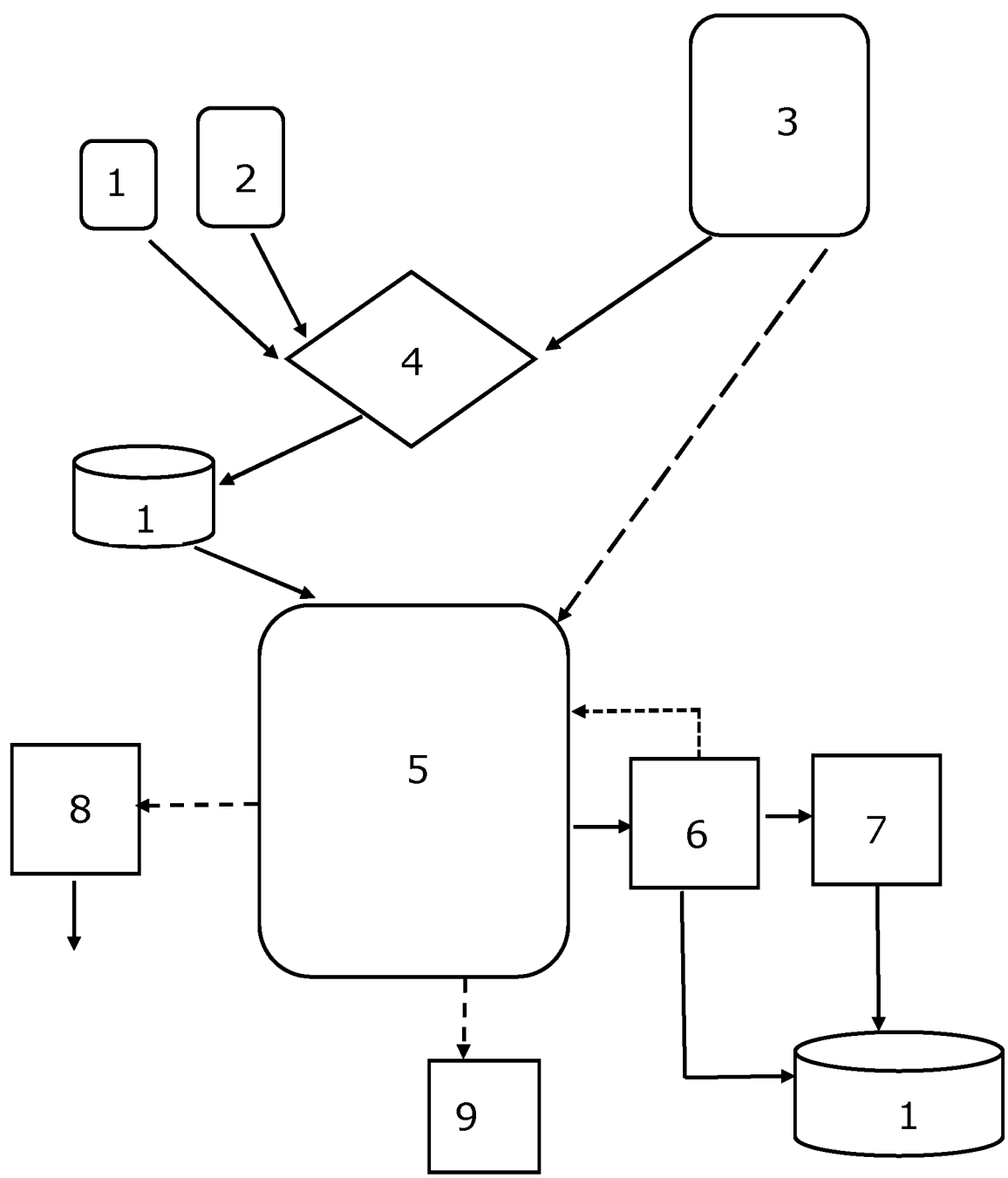
FIG. 2 is a schematic illustration of an alternative embodiment of the bioreactor system of the invention.

FIG. 2 shows an alternative embodiment of the bioreactor system illustrated in FIG. 1. In FIG. 2 there are two medium containers (1) and (2), for example where one medium container is for relatively highly soluble medium components and the other medium container is for poorly soluble medium components. The system can also include one or more additional medium containers (not shown) as desired. Concentrated medium from the two medium containers (1) and (2) enters the inline medium dilution system (4), where it is mixed with water or buffer from the water/buffer container (3).

FIG. 2 further shows an optional holding tank (11) inserted between the inline medium dilution system (4) and the cell culture vessel (5). The holding tank (11) may be used as necessary for temporarily holding diluted medium from the inline medium dilution system (4), and optionally to provide additional mixing of the diluted medium before it is led to the cell culture vessel (5).

All patent and non-patent references cited in the present application are hereby incorporated by reference in their entirety.

Any combination of the above-described elements in all possible variations thereof is encompassed by the invention unless otherwise indicated herein or otherwise clearly contradicted by context.

The terms "a", "an" and "the" as used herein are to be construed to cover both the singular and the plural, unless otherwise indicated or clearly contradicted by context.

What is claimed is:

1. A bioreactor system configured to continuously produce a product, said product selected from a cell, wherein said cell is selected from a bacterial cell, yeast or mammalian cell, and said bacterial cell is selected from an *E. coli* or *Bacillus* cell, and a biopolymer expressed by said cell, wherein the bioreactor system comprises:

a cell culture vessel (5);

a medium container (1;2);

a water and/or buffer supply (3);

an inline medium dilution system (4) for diluting concentrated medium from the medium container, the inline medium dilution system having an inlet and an outlet, wherein the inlet is in fluid communication with the medium container and the water/buffer supply, and wherein the outlet is in fluid communication with the culture vessel and further comprising a programmable logic controller that integrates operation and control of all components in said inline medium dilution system; and a product harvest module (6) for removing biopolymer, cells, impurities and cell medium, wherein said product harvest module is directly connected to said cell culture vessel (5) but not directly connected to said inline medium dilution system (4).

2. The bioreactor system of claim 1, further comprising a sensor connected to the inline medium dilution system, wherein the sensor is located within or outside the cell culture vessel which sensor can measure the concentration or the amount of medium or the amount of selected components or nutrients in the cell culture vessel.

3. The bioreactor system of claim 1, comprising an impurity filter unit (8) connected to said cell culture vessel but not directly connected to said inline medium dilution system.

4. The bioreactor system of claim 1, wherein the inline medium dilution system contains conductivity and/or pH process analyzers.

5. The bioreactor system of claim 1, wherein the medium container has a volume of at least 50 L.

6. The bioreactor system of claim 1, comprising at least two medium containers, each medium container being in fluid communication with an inlet of the inline medium dilution system.

7. The bioreactor system according to claim 1, wherein said bioreactor system is a chemostat or perfusion bioreactor system.

8. A method for producing a biopolymer using the bioreactor system according to claim 1, the method comprising:
(a) fermenting cells expressing the biopolymer in a suitable medium under suitable conditions to allow expression of the biopolymer by the cells,
(b) harvesting the biopolymer by removing medium comprising biopolymer and impurities via the product harvest module, and
(c) isolating the biopolymer from the harvested medium; wherein, during fermentation, the method further comprises: adding concentrated medium from a medium container and water or buffer from the water/buffer supply to an inlet of the inline medium dilution system to result in diluted medium, and feeding the diluted medium containing nutrients to the culture vessel through an outlet to replenish nutrients consumed by the cells and to compensate for medium removed for harvesting of the biopolymer.

9. The method according to claim 8, wherein concentrated medium in the medium container is diluted at least by a factor of at least two with water or buffer before being fed to the culture vessel.

10. The method according to claim 8, wherein concentrated medium from at least two medium containers is mixed with water or buffer prior to being fed to the culture vessel.

11. The method according to claim 8, wherein the cell density in the cell culture vessel during the fermentation reaches at least 10 million cells per ml medium.

12. The method according to claim 8, wherein concentrated medium is mixed with water/buffer and the concentrated medium in the medium container(s) is kept at a reduced temperature of below room temperature, wherein the concentrated medium has been pre-heated, or wherein the diluted medium is pre-heated from a reduced temperature of below room temperature prior to being added to the culture vessel.

13. The method according to claim 8, wherein the cells are mammalian cells.

14. The method according to claim 13, wherein the mammalian cells are selected from the group consisting of CHO (Chinese hamster ovary) cells, hybridomas, BHK (baby hamster kidney) cells, myeloma cells, HEK-293 cells, PER.C6® cells, human lymphoblastoid cells and NS0 cells.

15. The method according to claim 8, wherein the biopolymer is a polypeptide or protein.

16. The method according to claim 15, wherein the polypeptide or protein, is selected from an antibody or antibody fragment, a blood clotting factor, a cytokine, an enzyme or a peptide hormone; or a virus particle or part thereof.

17. The method according to claim 8, wherein concentrated medium in the medium container is diluted at least by a factor of at least three with water or buffer before being fed to the culture vessel.

18. The method according to claim 8, wherein concentrated medium in the medium container is diluted at least by a factor of at least four with water or buffer before being fed to the culture vessel.

19. The method according to claim 8, wherein concentrated medium in the medium container is diluted at least by a factor of at least five with water or buffer before being fed to the culture vessel.

20. The method according to claim 8, wherein the cell density in the cell culture vessel during the fermentation reaches at least 20 million cells per ml medium.

21. The method according to claim 8, wherein the cell density in the cell culture vessel during the fermentation reaches at least 30 million cells per ml medium.

22. The method according to claim 8, wherein the cell density in the cell culture vessel during the fermentation reaches at least 40 million cells per ml medium.

23. The method according to claim 8, wherein concentrated medium is mixed with water/buffer and the concentrated medium in the medium container(s) is kept at a reduced temperature of below 10° C., wherein the concentrated medium has been pre-heated, or wherein the diluted medium is pre-heated from a reduced temperature of below room temperature.

24. The method according to claim 8, wherein concentrated medium is mixed with water/buffer and the concentrated medium in the medium container(s) is kept at a reduced temperature of below 5° C., wherein the concentrated medium has been pre-heated, or wherein the diluted medium is pre-heated from a reduced temperature of below room temperature.

25. A bioreactor system configured to continuously produce a product, said product selected from a cell, wherein said cell is selected from a bacterial cell, yeast or mammalian cell and wherein said bacterial cell is selected from an *E. coli* or *Bacillus* cell, and a biopolymer expressed by said cell, wherein the bioreactor system comprises:

a cell culture vessel (5);

a product harvest module (6) for removing biopolymer, cells, impurities and cell medium, wherein said product harvest module is connected to said cell culture vessel but not directly connected to an inline dilution system (4);

a medium container (1;2);

a water and/or buffer supply (3); and an inline medium dilution system (4) for diluting concentrated medium from the medium container, the inline medium dilution system having an inlet and an outlet, wherein the inlet is in fluid communication with the medium container and the water/buffer supply, and wherein the outlet is in fluid communication with the culture vessel, and further comprising a sensor connected to the inline medium dilution system, wherein the sensor is located within or outside the cell culture vessel which sensor can measure the concentration or the amount of medium or the amount of selected components or nutrients in the cell culture vessel and instrumentation for monitoring and controlling the dilution process.

26. The bioreactor system according to claim 25, wherein said instrumentation for monitoring and controlling the dilution process is selected from the group consisting of a mass flow meter and analytical instrument selected from pH, conductivity and near-infrared instrumentation.

27. The bioreactor system according to claim 1, wherein said bioreactor system further comprises a bleed outlet connected to said cell culture vessel (5).

28. The bioreactor system according to claim 1, wherein the medium container has a volume of at least 100 L.

29. The bioreactor system according to claim 25, wherein said bioreactor system further comprises a bleed outlet connected to said cell culture vessel (5).

30. A non-photobiotic bioreactor system configured to continuously produce a product, said product selected from a cell and a biopolymer expressed by a cell, wherein the bioreactor system comprises:

a cell culture vessel (5);

a medium container (1;2);

a water and/or buffer supply (3);

an inline medium dilution system (4) for diluting concentrated medium from the medium container, the inline medium dilution system having an inlet and an outlet, wherein the inlet is in fluid communication with the medium container and the water/buffer supply, and wherein the outlet is in fluid communication with the culture vessel and further comprising a programmable logic controller that integrates operation and control of all components in said inline medium dilution system; and a product harvest module (6) for removing biopolymer, cells, impurities and cell medium, wherein said product harvest module is directly connected to said cell culture vessel (5) but not directly connected to said inline medium dilution system (4).

31. A non-photobiotic bioreactor system configured to continuously produce a product, said product selected from a cell and a biopolymer expressed by a cell, wherein the bioreactor system comprises:

a cell culture vessel (5);

a medium container (1;2);

a water and/or buffer supply (3); and an inline medium dilution system (4) for diluting concentrated medium from the medium container, the inline medium dilution system having an inlet and an outlet, wherein the inlet is in fluid communication with the medium container and the water/buffer supply, and wherein the outlet is in fluid communication with the culture vessel, and further comprising a sensor connected to the inline medium dilution system, wherein the sensor is located within or outside the cell culture vessel which sensor can measure the concentration or the amount of medium or the amount of selected components or nutrients in the cell culture vessel and instrumentation for monitoring and controlling the dilution process and a product harvest module (6) for removing biopolymer, cells, impurities and cell medium, wherein said product harvest module is connected to said cell culture vessel but not directly connected to said inline dilution system.

\* \* \* \* \*